(12) United States Patent
Wampler et al.

(10) Patent No.: US 6,264,635 B1
(45) Date of Patent: *Jul. 24, 2001

(54) ACTIVE MAGNETIC BEARING SYSTEM FOR BLOOD PUMP

(75) Inventors: Richard K. Wampler, Granite Bay; David M. Lancisi, Folsom, both of CA (US)

(73) Assignee: Kriton Medical, Inc., Sacramento, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/204,795

(22) Filed: Dec. 3, 1998

(51) Int. Cl.$^7$ .................................................... A61M 37/00
(52) U.S. Cl. ...................... 604/151; 604/131; 417/423.1; 417/423.7
(58) Field of Search .................................... 604/151, 131, 604/500; 417/423.1, 423.7, 423.12, 203, 206

(56) References Cited

U.S. PATENT DOCUMENTS

| | | |
|---|---|---|
| 3,572,982 | 3/1971 | Kozdonsohn . |
| 4,876,492 | 10/1989 | Lester et al. . |
| 4,880,362 | 11/1989 | Laing et al. . |
| 5,049,134 | 9/1991 | Golding et al. . |
| 5,197,865 | 3/1993 | Sevrain et al. . |
| 5,350,283 | 9/1994 | Nakazeki et al. . |
| 5,591,017 | 1/1997 | Dwyer . |
| 5,692,882 | 12/1997 | Bozeman, Jr. et al. . |
| 5,695,471 | 12/1997 | Wampler . |
| 5,725,357 | 3/1998 | Nakazeki et al. . |
| 5,728,154 | 3/1998 | Crossett et al. . |
| 5,738,503 | 4/1998 | Schmidt-Marloh et al. . |
| 5,840,070 | 11/1998 | Wampler et al. . |

FOREIGN PATENT DOCUMENTS 41 02 707   8/1991   (DE) .
WO8807842 * 10/1988   (WO) .
WO 98 11650   3/1998   (WO) .

OTHER PUBLICATIONS

C. Peter Cho et al.; Eddy Current Loss Calculation in the Permanent Magnet of a Large Horse Power Axial–Field Motor; Jun. 14, 1994; Proceedings, Twenty–third Annual Symposium, Incremental Motion Control Systems & Devices, pp. 245–253.

C. Peter Cho et al.; Cogging Torque Reduction, Axial Force Variation, and Output Torque Effect of a High–Power–Density, Axial Field, Brushless, Permanent Magnet Motor; Jun. 6, 1995; Proceedings, Twenty–fourth Annual Symposium, Incremental Motion Control Systems & Devices, pp. 297–307.

C. Peter Cho et al.; Feasibiltiy Study of a Novel Integrated Electric Motor/Pump for Underwater Applications; Jun. 6, 1995; Proceedings, Twenty–sixth Annual Symposium, Incremental Motion Control Systems & Devices, pp. 309–316.

C. Peter Cho et al.; Ongoing Feasibility Study of a Novel Integrated Electric Motor/Pump Concept; Jun. 11, 1996; Proceedings, Twenty–fifth Annual Symposium, Incremental Motion Control Systems & Devices, pp. 51–62.

C. Peter Cho et al.; Energy Losses in Magnetic Lamination Materials of a Novel Integrated Motor/Pump System; Jul. 22, 1997; Proceedings, Twenty–sixth Annaul Symposium, Incremental Motion Control Systems & Devices, pp. 325–333.

* cited by examiner

Primary Examiner—John D. Yasko
(74) Attorney, Agent, or Firm—George H. Gerstman; Seyfarth Shaw

(57) ABSTRACT

An implantable rotary blood pump including a rotor mounted for rotation within a pump housing. The rotor has a shaft portion and an impeller carried by the shaft portion. A rotor motor is provided, with the motor including a plurality of permanent magnets carried by the impeller and motor stators on opposite sides of the impeller. The motor is operable to transmit torque and also to provide an axial magnetic force that acts as an axial bearing.

15 Claims, 9 Drawing Sheets

ACTIVE MAGNETIC BEARING SYSTEM FOR BLOOD PUMP

FIELD OF THE INVENTION

The present invention concerns blood pumps. More specifically, the invention pertains to continuous flow pumps of rotary design, which may be suitable for installation in humans, for use as chronic ventricular assist devices.

BACKGROUND OF THE INVENTION

In Wampler U.S. Pat. No. 5,695,471, a continuous flow pump of rotary design is disclosed, suitable for permanent implantation in humans, for use as a chronic ventricular assist device. The disclosed device uses passive, magnetic radial bearings to maintain an impeller and its support shaft for rotation about an axis, thus eliminating the necessity for a drive shaft seal.

Typically prior art blood pumps use mechanical bearings to support the rotor with respect to the stator. The use of hydrodynamic thrust bearings has been disclosed for aiding in preventing thrombosis. However, blood cell damage and various other problems may be created by the use of hydrodynamic thrust bearings and mechanical bearings and it is desirable for a blood pump to use a magnetically suspended rotor if possible. However, a problem associated with magnetically suspending the rotor is that movement of the pump may result in movement of the rotor in the axial direction, causing the rotor or the impeller to contact a part of the pump casing. It is highly undesirable in a blood pump construction to have any continuing contact between the impeller and a part of the blood pump casing.

In Wampler U.S. Pat. No. 5,695,471, there is disclosed the shuttling back and forth of the rotor assembly with each cardiac cycle of the user, in order to prevent thrombosis. If this axial shuttling would not happen naturally, it would be desirable to have a system in which it could be induced electromagnetically.

In Wampler U.S. application Ser. No. 08/910,375, filed Aug. 13, 1997, now U.S. Pat. No. 5,840,070, the use of hydrodynamic bearings in an implantable blood pump is disclosed. With the hydrodynamic bearings, there is a frictional engagement which has to be overcome before the hydrodynamic bearings can be fully effective. The frictional engagement is a result of a preload that is applied by the front loading of the magnetic bearing. Thus an initial starting force is required that will enable the initial frictional engagement to be overcome. This initial starting force can create difficulties, and it would be advantageous to avoid its necessity.

Due to the preload of the negative axial spring rate of the passive radial magnetic bearings of the rotor, there is an axial magnetic force urging the impeller rearward against the casing. In view of the foregoing, it would be advantageous to be able to manipulate the axial force on the impeller during the starting of the pump.

There have been attempts to alleviate the starting axial force problem by having suspended systems using electromagnets. Typically in such systems, a dedicated electromagnetic control system is used to control the position of the impeller. There would be separate dedicated electronic controls and electromagnets for controlling the position of the rotor and the impeller. However, these separate dedicated electronic controls and electromagnets add to the weight, volume and complexity of the system.

It is, therefore, an object of the present invention to provide a rotary blood pump in which the rotor is magnetically suspended.

Another object of the present invention is to provide a rotary blood pump in which contact between the impeller and the blood pump housing is avoided.

A still further object of the present invention is to provide a novel rotary blood pump in which the axial forces on the impeller may be controlled.

An additional object of the present invention is to provide a novel rotary blood pump in which the axial position of the impeller may be controlled in an efficient manner.

Another object of the present invention is to provide a novel rotary blood pump that is small, light, simple in construction, and relatively easy to manufacture.

Other objects and advantages of the present invention will become apparent as the description proceeds.

SUMMARY OF THE INVENTION

In accordance with the present invention, a rotary blood pump is provided. The pump comprises a pump housing and a rotor mounted for rotation within the housing. The rotor has a shaft portion and an impeller carried by the shaft portion. A rotor motor is provided. The motor includes a plurality of permanent magnets carried by the impeller and a motor stator including electrically conductive coils and pole pieces located within the housing. The motor is operable to transmit torque and also to provide an axial magnetic force that acts as an axial bearing.

In the illustrative embodiment, the rotary blood pump includes passive radial magnetic bearings carried by the shaft portion and radial magnetic bearings carried by the housing. A sensor is provided for detecting axial deflection of the impeller and a circuit is provided for energizing the stator in response to the detector.

In the illustrative embodiment, there is a first motor stator positioned on one side of the impeller and a second motor stator positioned on an opposite side of the impeller. The motor stators each include electrically conductive coils and pole pieces located within the housing. A detector senses the axial position of the impeller. If the axial position is neutral, then current to the stators is not varied. However, if the axial position is other than neutral the relative currents to the first and second stators are varied to provide an axial force to return the impeller to neutral.

A more detailed explanation of the invention is provided in the following description and claims, and is illustrated in the accompanying drawings.

DETAILED DESCRIPTION OF THE ILLUSTRATIVE EMBODIMENT

The present invention preferably utilizes two stators, each on opposite sides of the impeller and each having a number of stator coils and pole pieces. One example of an implantable heart pump with two stators is the FIGS. 11–14 embodiment of Wampler application Ser. No. 08/910,375, filed Aug. 13, 1997, now U.S. Pat. No. 5,840,070, the disclosure of which is incorporated herein. It is understood, however, that no limitation is intended with respect to the particular heart pump to which the present system is applicable.

Figure 1:
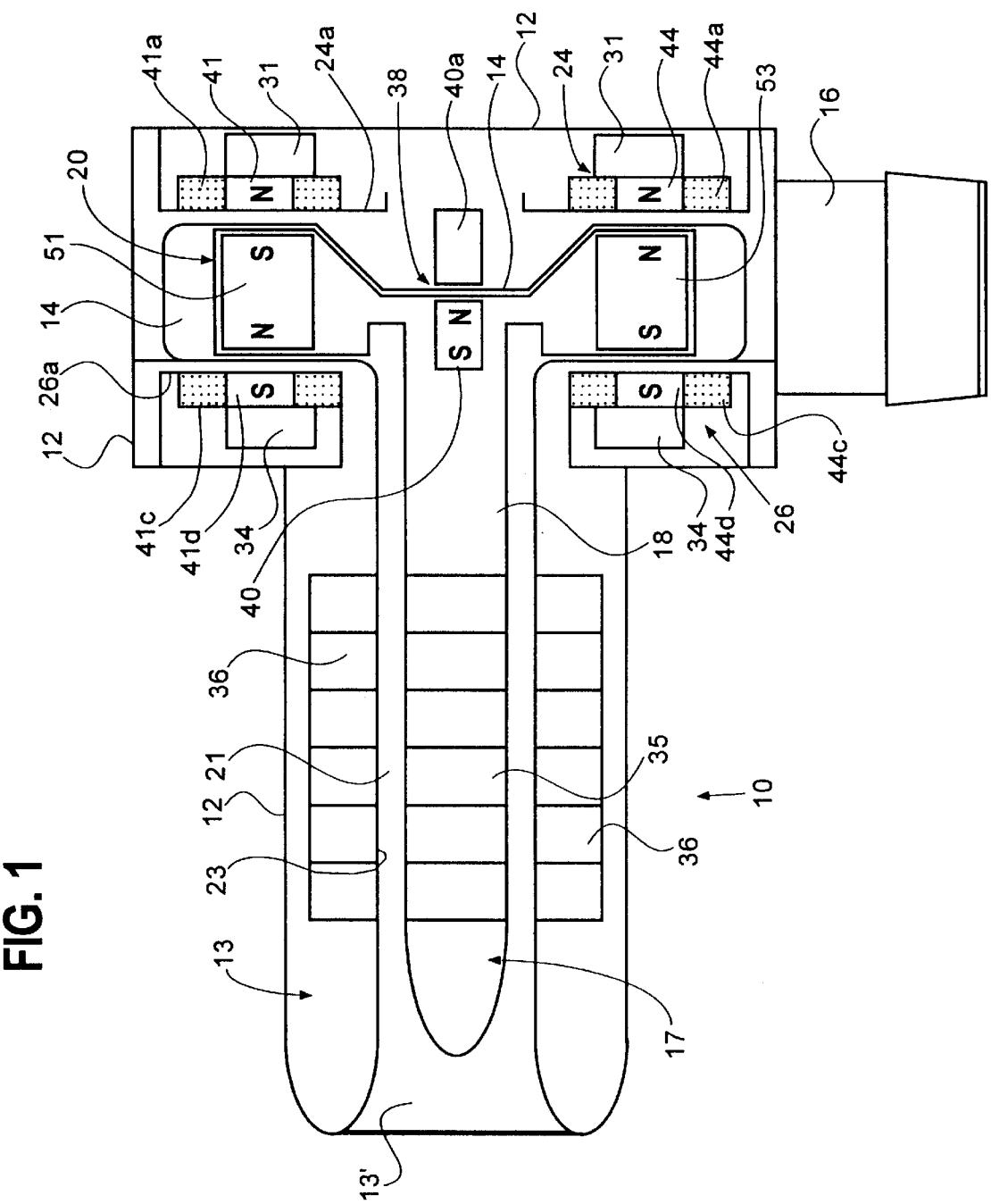
FIG. 1 is a longitudinal, cross-sectional view of a pump constructed in accordance with the principles of the present invention.

As illustrated in FIG. 1, a rotary blood pump 10 includes housing 12, having an elongated inlet tube 13 with an entry end 13' and an impeller casing or volute 14. A discharge tube 16 extends through the housing to communicate with the interior periphery of casing 14. Tube 16 has a tangential orientation with respect to the radius of the casing 14, for effectively channeling the blood output from the pump.

A pump rotor 17 is located within housing 12 and includes a support shaft 18 attached to an impeller 20. There is a blood flow path 21 between a rotor 17 and the inner sidewalls 23 of inlet tube 13.

Rotor 17 is mounted for rotation about a longitudinal axis which extends both through shaft 18 and impeller 20. Although this embodiment includes an impeller and a casing of centrifugal design, the present invention may also be adapted advantageously to rotary blood pumps of axial flow design or other types of rotary blood pumps.

Impeller 20 has a number of blade sectors that are relatively thick in the axial direction. The thick impeller 20 has the ability to utilize magnetic pieces 51 and 53 that are inserted in a manner enabling a pair of stators 24 and 26 to be on opposite sides of the impeller. A first motor stator 24, comprising conductive coils or motor windings 41a, 44a, pole pieces 44, 41 and back iron 31, is located at the rear of impeller 20 on a wall 24a. A second motor stator 26, comprising windings 41c, 44c, pole pieces 41d, 44d, and back iron 34, is positioned on the forward side of impeller 20 on a wall 26a: Although (for simplicity) only two coils and two pole pieces are illustrated on each side of the impeller in FIG. 1, it is to be understood that in the embodiment illustrated in FIGS. 2–9, six windings and pole pieces are on each side of the impeller.

Magnetic bearings 35 are provided on the rotor 17 and magnetic bearings 36 are on the casing 14 for levitating rotor 17 and maintaining it in proper radial alignment with respect to its longitudinal axis.

A hall sensor 38 comprising a magnet 40 along the axis of the impeller 20 and carried by the impeller 20 and a coaxial sensing element 40a between the impeller and the housing 20 is provided for detecting and measuring axial movement of the impeller. The hall sensor 38 provides a real time measurement of the axial position of the rotor 17 relative to the stators 24, 26 and is part of a stator control circuit for varying the current to the motor coils 41a, 44a, 41c, 44c, in response to measured changes in position of the impeller 20, in order to apply an axial restoring force to the rotor 17.

It is to be understood that various other devices may be utilized for measuring the axial position of the rotor 17 relative to the stators 24, 26. For example, the impeller 20 may carry a magnet along its axis at its distal end and the casing 14 may also have a force transducer responsive to the distance of the magnet for providing a signal reflective of that distance. Various position sensors may be utilized as desired.

As discussed in more detail below, when the stators function to transmit torque, the stator windings 41a, 44a, 41c, 44c are energized to produce equal opposing axial forces on the magnets 51, 53. For example, windings 44a and 44c are producing electromagnets which are repelling the adjacent magnet face, i.e., north to north and south to south. Similarly, windings 41a and 41c are producing electromagnets which are attracting the adjacent magnet faces, i.e., north to south and south to north. These represent the two conditions in which the coils on each side of the magnet can act synergistically to produce torque.

During normal operation, the net axial force of the stator coils acting on the magnets is zero, provided that the magnets are axially centered between the stators. An imbalance in the current delivered to the coils will result in an imbalance in the electromagnetic forces produced by the stator coils and, an imbalance in the axial force on the rotor. Torque will not be affected. As discussed below, this imbalanced force is exploited as a restoring force. Thus axial restoring forces are applied to the rotor by controlling the balance of the current in the opposed stator coils. To this end, the stators are controlled in parallel so that the current applied to the coils is adjusted to produce the necessary restoring force on the rotor. The control of the restoring force is determined by the position of the rotor assembly as measured by the hall sensor or other type of position sensor.

The phasing of the restoring force, with respect to the torque angle of the motor, may be accomplished in several ways. One way would be to alter only the current balance between the two coils but to keep the phasing of the current the same.

Another approach would be to apply a current pulse out of phase with the torque-producing current. In doing this, the restoring current pulse would act when it had the greatest affect on the axial position and the least contribution to torque. This strategy preferably utilizes individual control of each coil in order to achieve the desired effect.

In an illustrative embodiment of the invention, the motor has six poles 41, 42, 43, 44, 45 and 46 in the stator and four poles (magnets) 51, 52, 53 and 54 in the rotor, although other combinations of motor poles and stator configurations may be utilized. FIGS. 2–6 comprise diagrammatic representations of four arc-shaped segments which represent the motor rotor and six arc-shaped segments which represent stator coils or windings. The six coils 41a, 42a, 43a, 44a, 45a and 46a are wired in three phases in a wye configuration or a delta configuration, such that, at any moment, two phases (four coils) are energized and the remaining phase (two coils) are not energized.

In FIGS. 2–6, coils 43a and 46a are phase A coils, coils 42a and 45a are phase B coils, and coils 41a and 44a are phase C coils. Although FIGS. 2–6 represent only a single stator motor, the principle for the double stator is the same. The stator is illustrated to visualize the resulting electromagnetization produced by the current in the energized coil. Phase A is magnetized to south and phase C to north. Thus there are two north and two south poles. The south poles are 180° apart and the north poles are 180° apart.

Phase B is not energized and has no electromagnetic pole. This represents one commutation state of the stator. There are a total of six commutation state combinations for a three phase motor. The motor control logic rotates the "wave" of magnetization around the stator in synchrony with the magnets as they spin in order to maintain torque. The commutation is done with back emf sensing. The rotor position is found from the back emf signal and the phases are automatically switched to keep positive torque enabling the motor to run continually. Twelve commutations represent a 360° rotation.

The system for producing an axial restoring force using the stator windings is diagrammatically illustrated in FIGS.

Figure 2:
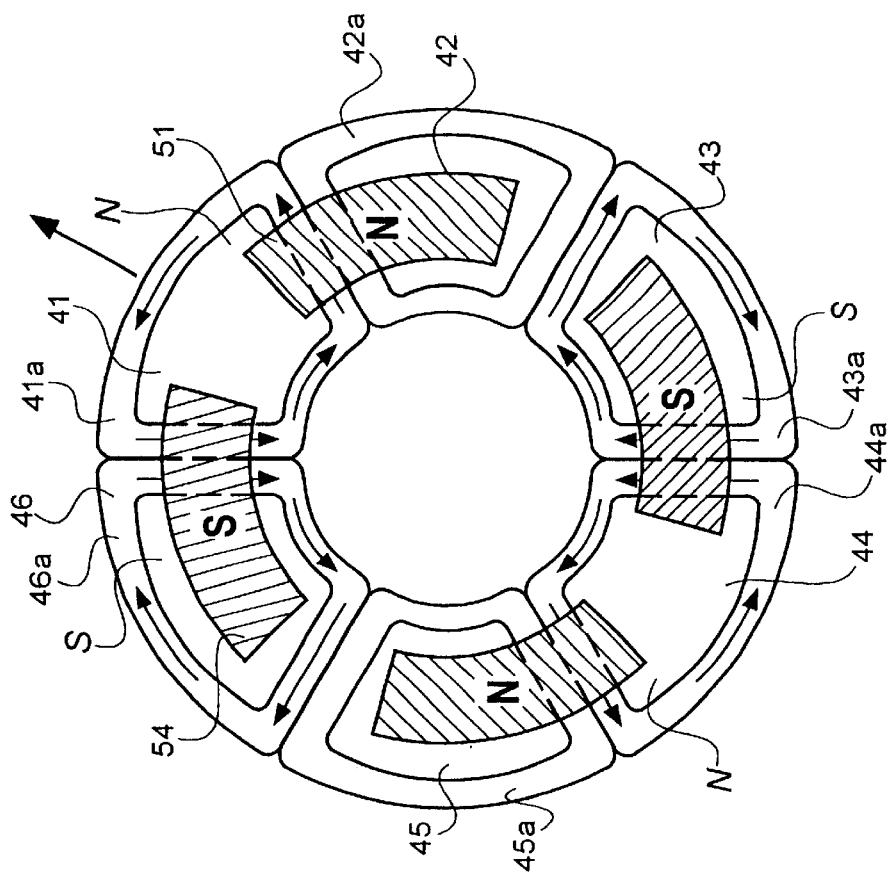
FIGS. 2–6 are diagrammatic views of various stator pole and rotor magnet positions, with arrows indicating the coil current direction.

2–6. Referring to FIG. 2, in which the rotor and stator are at a zero degrees position, magnet 51 is being repelled in the clockwise direction by pole 41 and magnet 54 is being repelled in the counterclockwise direction by pole 46. Since the magnets are placed symmetrically about the active stator poles, the resulting torque produced in this position is zero. The same situation exists for magnets 52 and 53 with respect to stator poles 43 and 44. This may be referred to as "unstable" equilibrium point.

Figure 3:
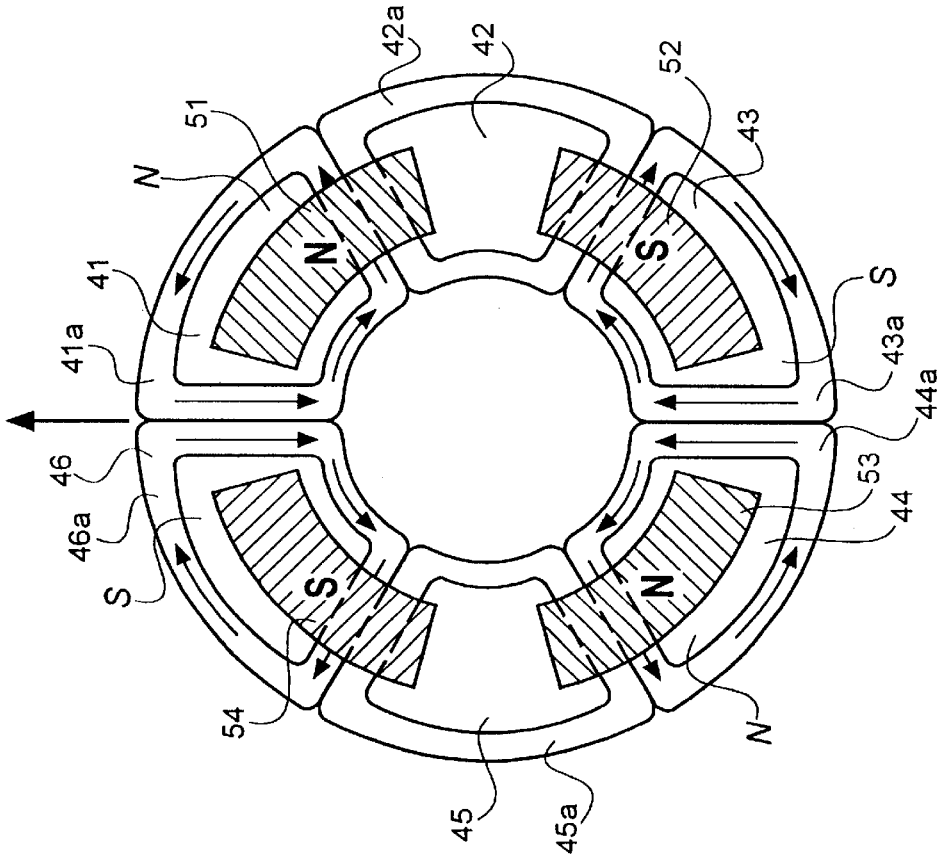

In FIG. 3, the rotor has been rotated clockwise 30°. Magnet 54 is now being repelled by pole 46 in the clockwise direction and stator pole 41 is repelling magnet 51 in the clockwise direction, producing clockwise torque. A torque of equal magnitude and in the clockwise direction is also being produced by the action between stator pole 43 and magnet 52 and stator pole 44 and magnet 53. This is useful torque although it is not maximum torque.

Figure 4:
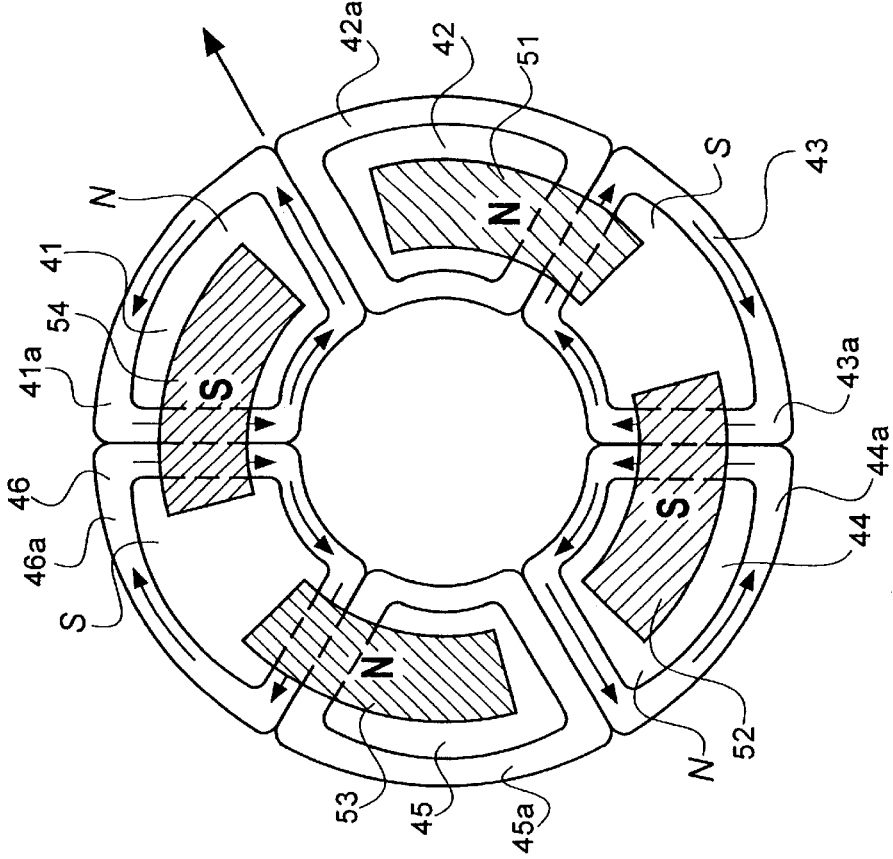

Now referring to FIG. 4 in which the rotor has been rotated clockwise to 45°. Magnet 54 is positioned exactly in the middle between stator pole 46 and stator pole 41. Stator pole 46 is repelling magnet 54 clockwise and stator pole 41 is attracting magnet 54 clockwise. Thus, there is a synergistic action producing clockwise torque. A torque of equal magnitude and in the clockwise direction is also being produced by the action between stator pole 43 and stator pole 44 and magnet 52. This corresponds to the point of maximum torque. Magnets 41 and 43 are directly over stator poles 52 and 55 (which do not have excitation current at this time). It should be noted that these diagrams represent only one stator, and that there is a mirror image of this relationship on the other end of the magnets in which all of the magnetic poles are switched to produce synergistic torque.

Figure 5:
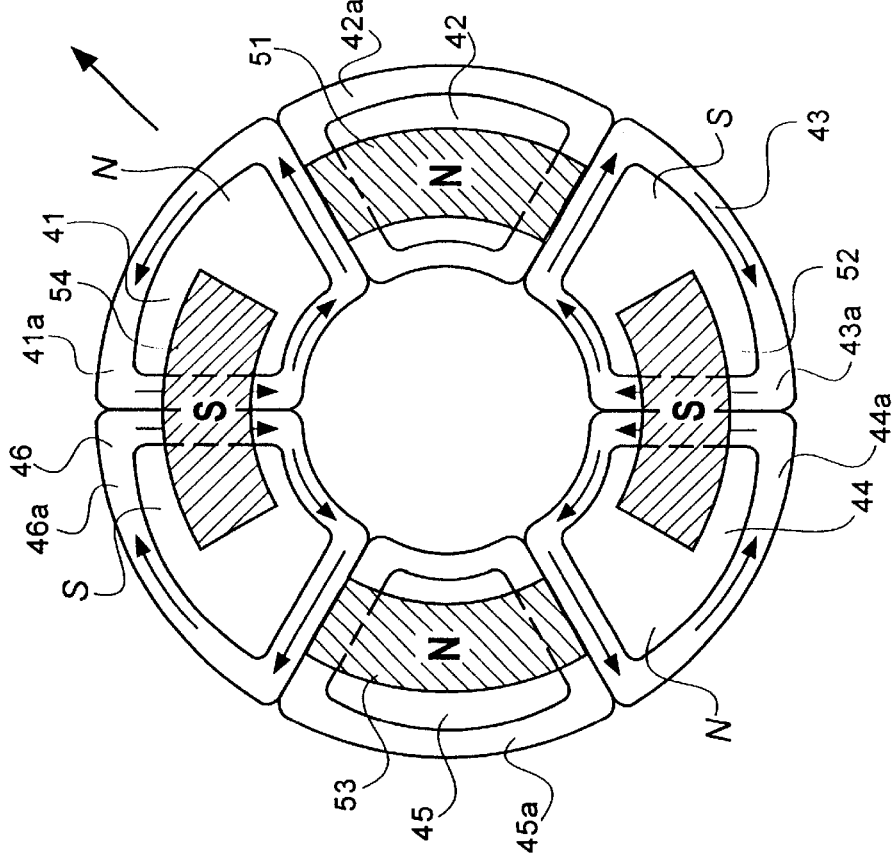

In FIG. 5, the rotor has been rotated clockwise to 60°. Magnet 51 is being attracted by stator pole 43 in the clockwise direction and magnet 52 is being repelled by stator pole 43 in the clockwise direction and attracted by stator pole 44 in the clockwise direction, thereby producing torque that is substantially equal to the torque that is produced at 30°.

Figure 6:
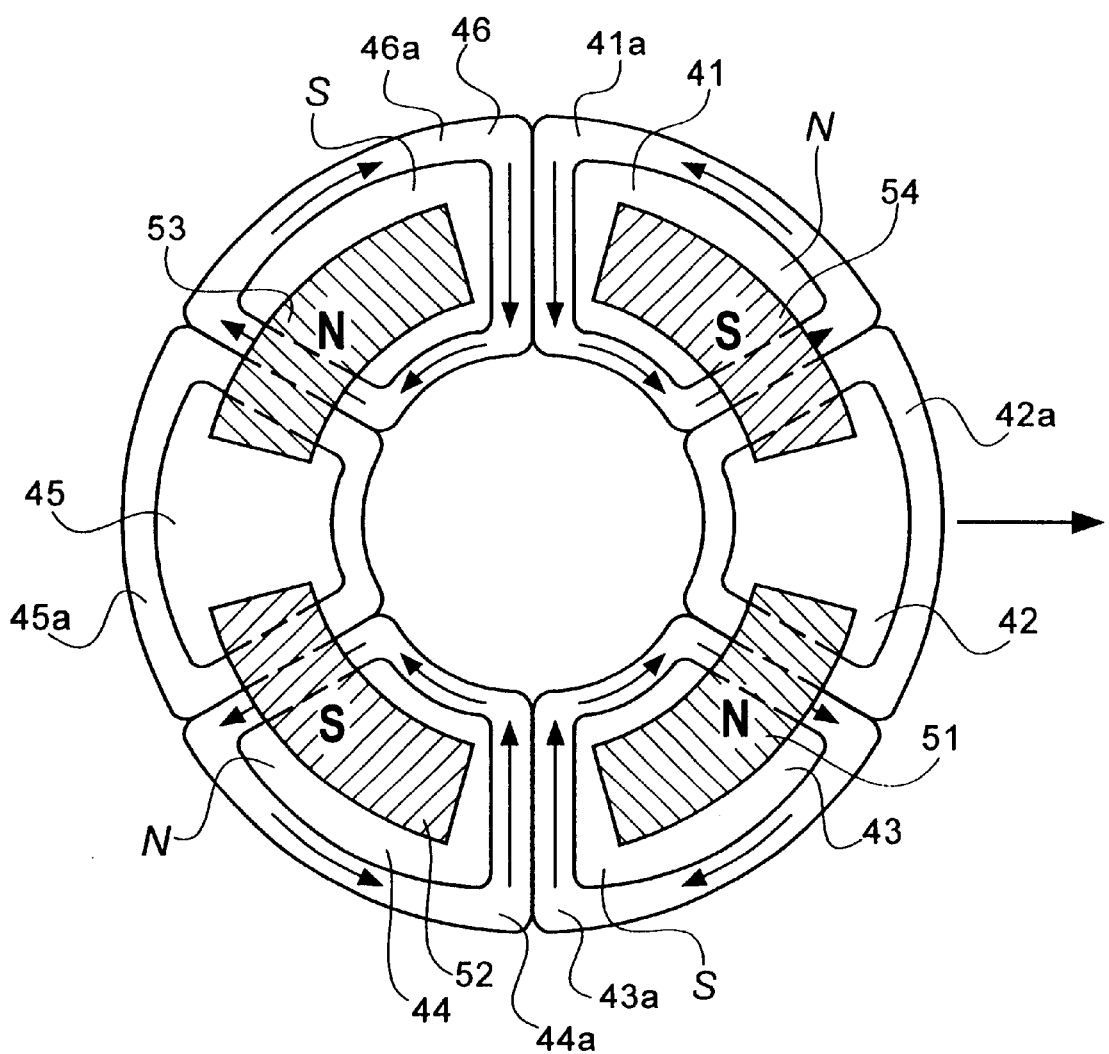

Now referring to FIG. 6 in which the rotor has been rotated clockwise to 90°, magnet 53 is being attracted by stator pole 46 in the clockwise direction and magnet 54 is being attracted to stator pole 41 in the counter clockwise direction. The forces are equal and opposite and no torque is produced. The same situation applies for magnets 51 and 52 and stator poles 43 and 44, respectively. This refers to the "stable" equilibreum point.

Figure 7:
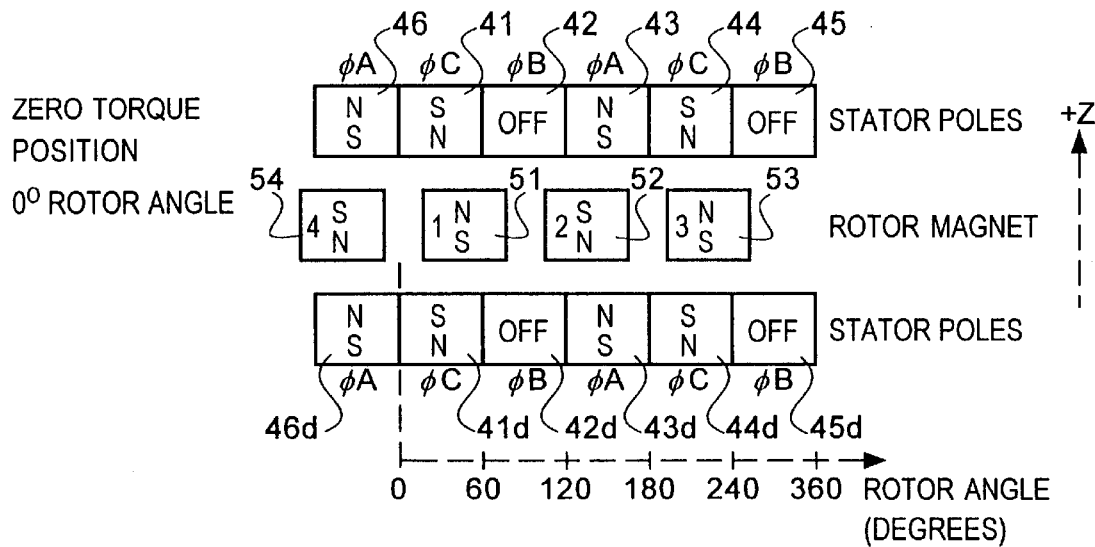
FIGS. 7, 8 and 9 are diagrammatic side views of the motor stators and rotor magnets at different angular positions.
Figure 8:
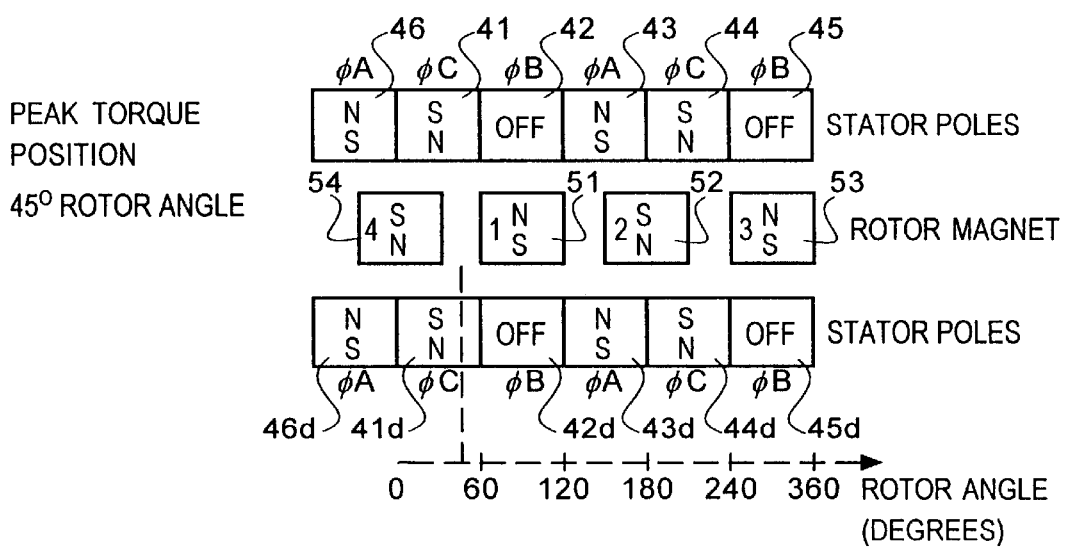
Figure 9:
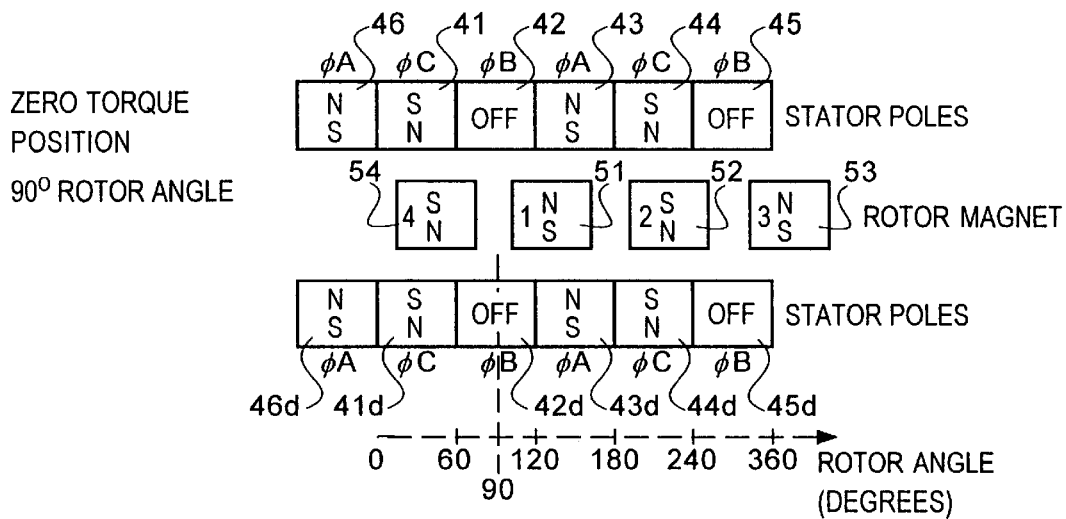

FIG. 7 is a side view of the motor unwrapped in the condition discussed above at zero degrees which produces no torque. In FIG. 8, there is a side view of the relationship which exists at 45° with maximum torque. FIG. 9 is a side view of the rotor at 90° rotation showing the torque to be zero again. If the magnet is precisely in the axial center between the two stator halves, and the current going to both the stators is equal, regardless of the rotational position of the rotor magnets or the sequence of excitation of the stator poles, the combination of magnetic attractive and repulsive forces will cancel each other out in the direction of the z axis, and there will be no net axial force. However, the action between the magnets and stator iron and poles is unstable and non-restoring. Thus, if the motor magnets are displaced in the positive z direction 0.005 inch for example, a force in the positive z direction will result. If a restoring force is not imposed, the magnets would not stop until they reached the housing or the stator iron. We have discovered that a magnetic restoring force can be provided by unbalancing the currents to the two stators, in order to return the magnets to the magnetic center.

As an example, (although no limitation is intended and the numbers could be other selected amounts), normally 26 ampere turns (AT) would go to each stator for a total of 52 AT acting on the motor magnets. In the first case (at zero degrees in FIG. 7) the magnets are being repelled by the stator poles in a restoring manner. This is, as the magnets are moved in the positive z direction they come closer to like poles of the upper stator and experience an increased force pushing them in the negative z direction. Likewise, the lower end of the magnets is moving further from the like poles of the lower stator and, thus, the action between them, pushing in the positive z direction is reduced. The same restoring dynamic would occur if the rotor magnets were deflected in the negative z direction. Changing the current balance between the two stators can increase this desirable restoring force. If the current in the upper stator is increased to 39 AT and the lower stator decreased to 13 AT, the restoring force will be increased. This is because the upper stator poles will repel with greater force in the negative z direction and the lower stator poles will repel with less force in the positive z direction. The torque produced will be the same since there will still be a total of 52 AT acting on the rotor.

In the case at 90 degrees in FIG. 9, where there is mutual attraction between the magnets and stator poles, the resulting force is not restoring in the z direction. If the rotor is displaced in the positive z direction, a force in the positive z direction will result. To counteract this force, one could lower the current going to the upper stator to 13 AT and increase the current in the lower stator to 39 AT. As a result of this change, there will be a decreased attraction in the positive z direction by the upper stator and an increase attraction in the negative z direction, which will act to bring the magnets back toward the neutral position. Note that the total ampere-turns to the stators are still 52 AT. Thus, the resulting torque is the same.

Figure 10:
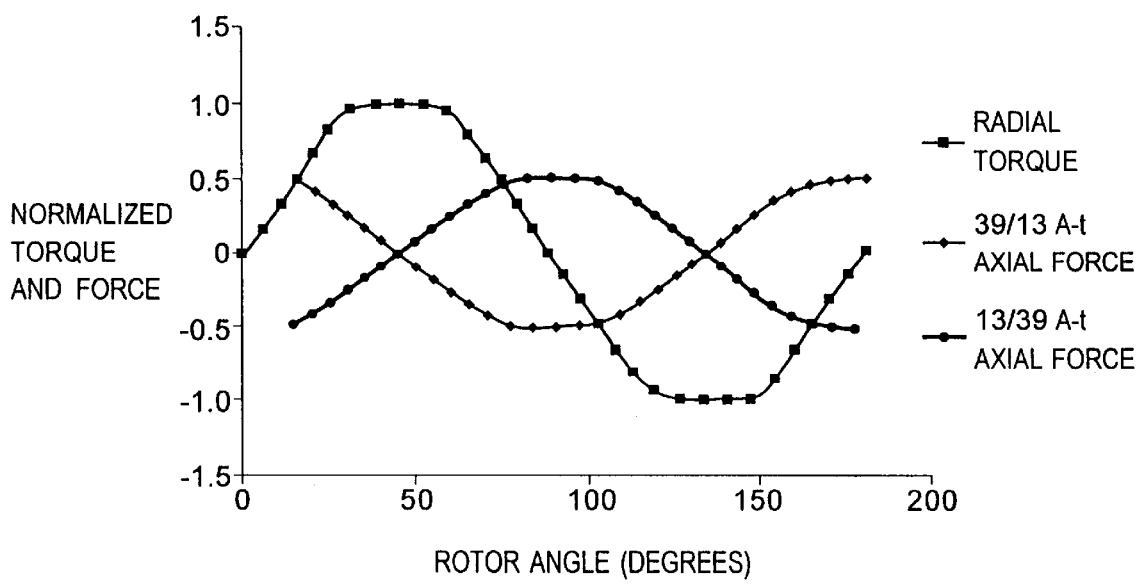
FIG. 10 is a graph illustrating the relationship between the radial torque and axial force versus the rotor angle.

The graph of FIG. 10 illustrates the relationship between the torque angle and the resulting axial force when the current to the stators is 13 AT in one and 39 AT in the other. The rotor magnets are located exactly half way between the two motor stators in the z-axis. This graph shows that a net axial force can be produced. The magnitude of the force is proportional to the difference in current supplied to the upper and lower stator and the rotor angular position. This provides a means of keeping the magnets in the center while still using normal excitation and by manipulating only the current distribution to the two stators.

Figure 11:
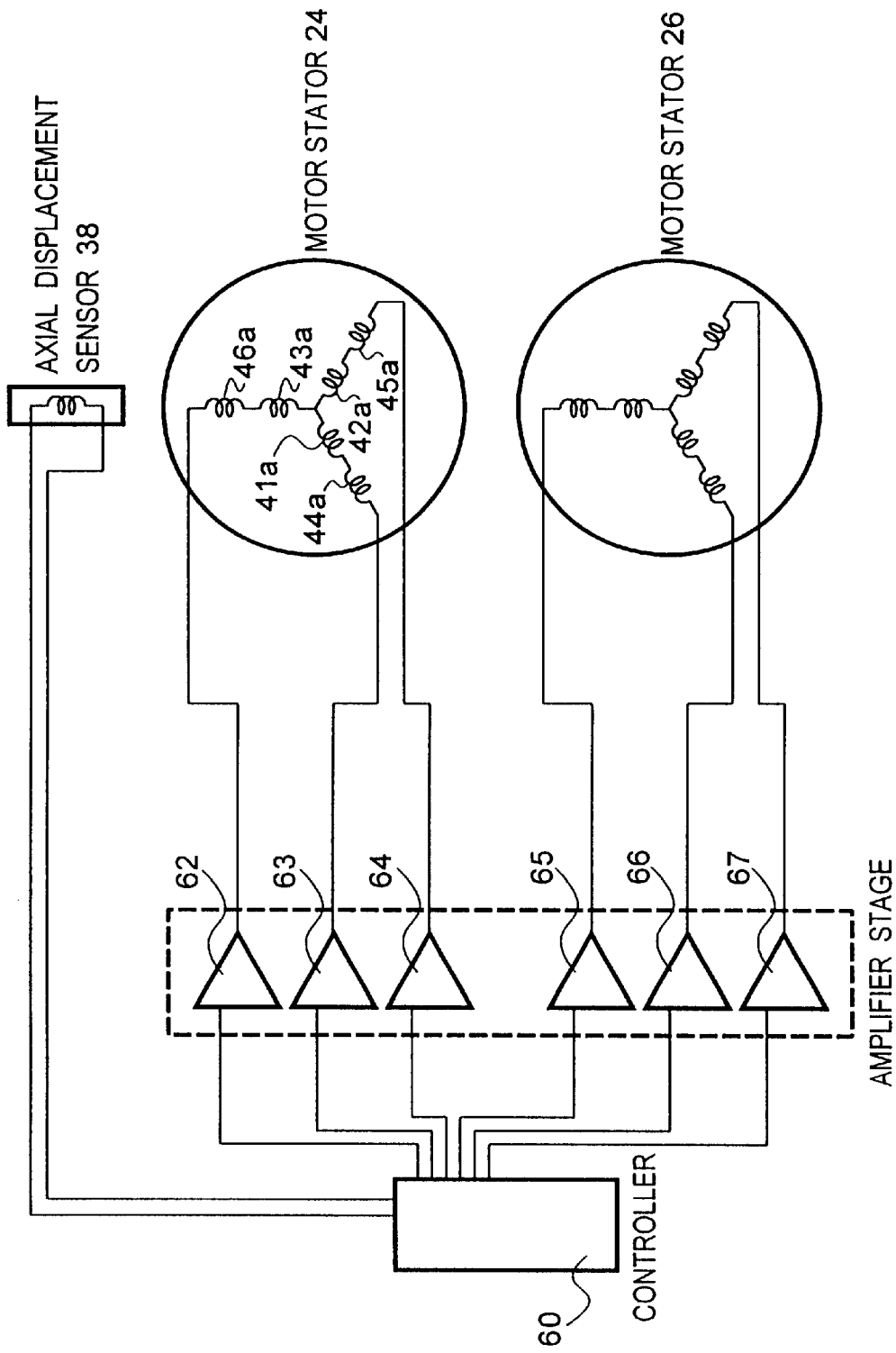
FIG. 11 is a schematic stator control circuit according to principles of the present invention.

An axial position sensor and algorithm and a controlling circuit is shown in the schematic of FIG. 11. A controller 60, which may include a microprocessor, operates in response to axial displacement sensor 38 to control the current through amplifier 62 to stator windings 46a and 43a; to control the current through amplifier 63 to windings 41a and 44a; to control the current through amplifier 64 to windings 42 and 45 of motor stator 24; and to control the currents through amplifiers 65, 66 and 67 to the respective windings of oppositely positioned motor stator 26. For the motor shown, there would be twelve zones in each revolution when a restoring force could be applied to the rotor magnets. The restoring force is a function of rotor angular position and at the peak torque point, there is little if any available axial force produced by the current imbalance in the stators.

Going back to the analog motor it can be seen that if the rotor is placed at the 45-degree position, magnets one and three are directly over the unexcited poles two and five. This can also be seen in FIG. 7. With individual stator pole control, energizing these poles (which are not usually energized at this time for producing torque) could create an additional restoring force. In this case it can be seen that the upper pole would repel in the negative z direction and the lower pole would attract, synergistically, in the negative z direction. No net torque would be produced by this action. By increasing the current to each pole, the restoring force would be increased proportionately. A schematic of the control scheme needed to produce a restoring force in this way is shown in FIG. 12.

Figure 12:
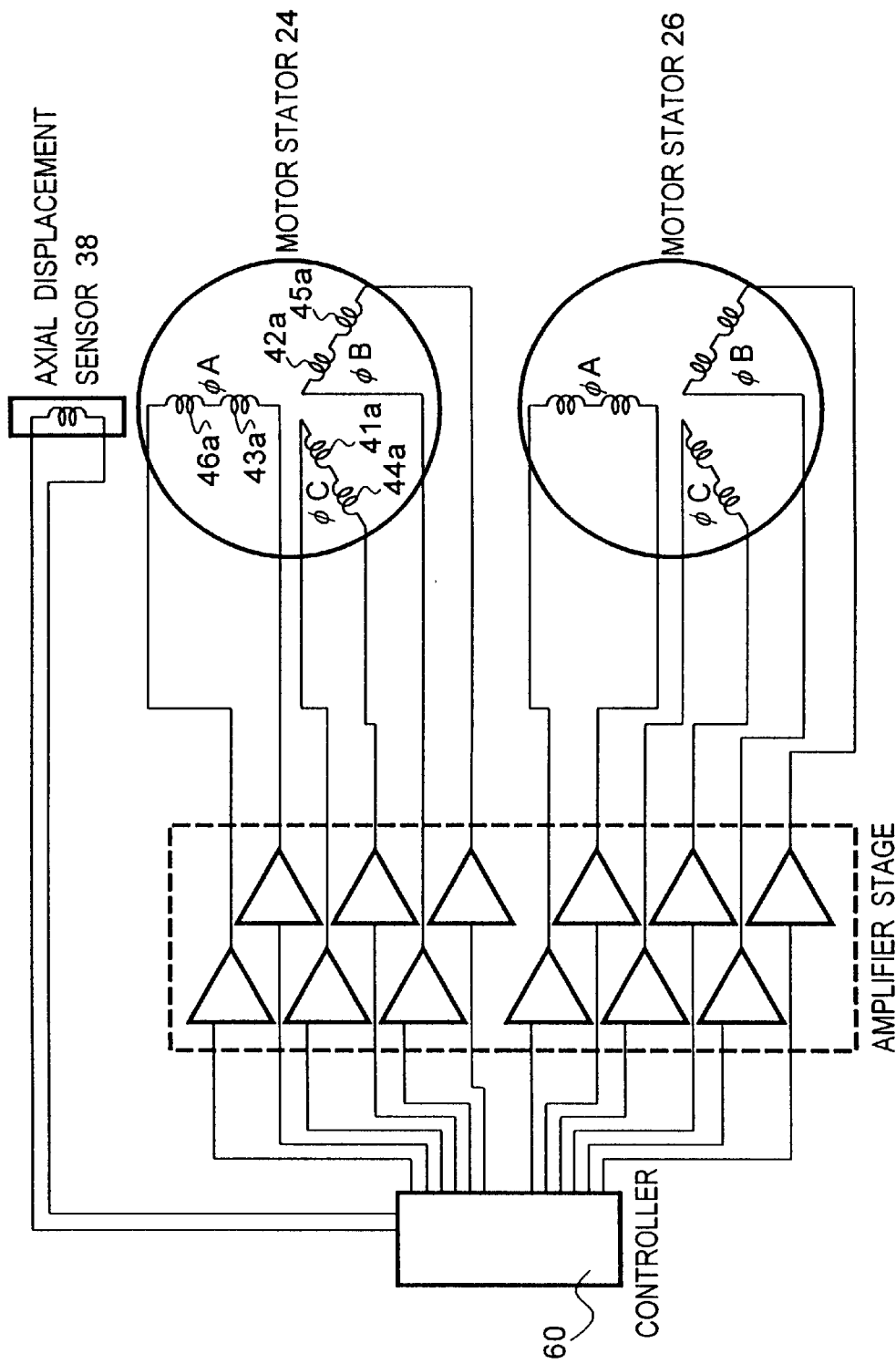
FIG. 12 is a schematic control circuit according to another embodiment of the present invention.

Referring to FIG. 12, controller 60 controls currents through a number of amplifiers, with each phase of windings having a pair of amplifiers for individual stator pole control.

The power requirements should be very low using the FIG. 11 strategy, in which the current balance between the two stators is adjusted. Since the current would still be generating torque, the increased power would be the result of the increased $I^2R$ losses in the stator coils. As an example, if the impedance of the excited phases in each stator is three ohms and the current is 0.5 amperes, the coil losses would be (0.25×3)+(0.25×3)=1.5 watts. If the current balance is changed such that one coil has 0.25 amperes and the other has 0.75 (corresponding to 13 AT and 39 AT, respectively) then the power would be (0.0625×3) (0.5625×3) =1.875 watts. The increased power would be 0.375 watts if it was necessary to unbalance the stator currents by the above ratio all of the time. It is unlikely that continuous excitation would be needed. This would not account for losses of the additional controller electronics needed to achieve the active control.

In the FIG. 12 embodiment in which the normally inactive stator poles are individually energized, the power used would not contribute to torque and would all be additional power and losses to the system. Since only one phase is being exited and since the currents would be equal and produce synergistic forces the power would be (0.25×3)= 0.75 watts, if these poles were excited all the time. Again, it is unlikely that they would be energized all the time.

Thus, a system for actively controlling the axial position using the coils of the stator poles for the production of torque and axial restoring forces is disclosed.

Figure 13:
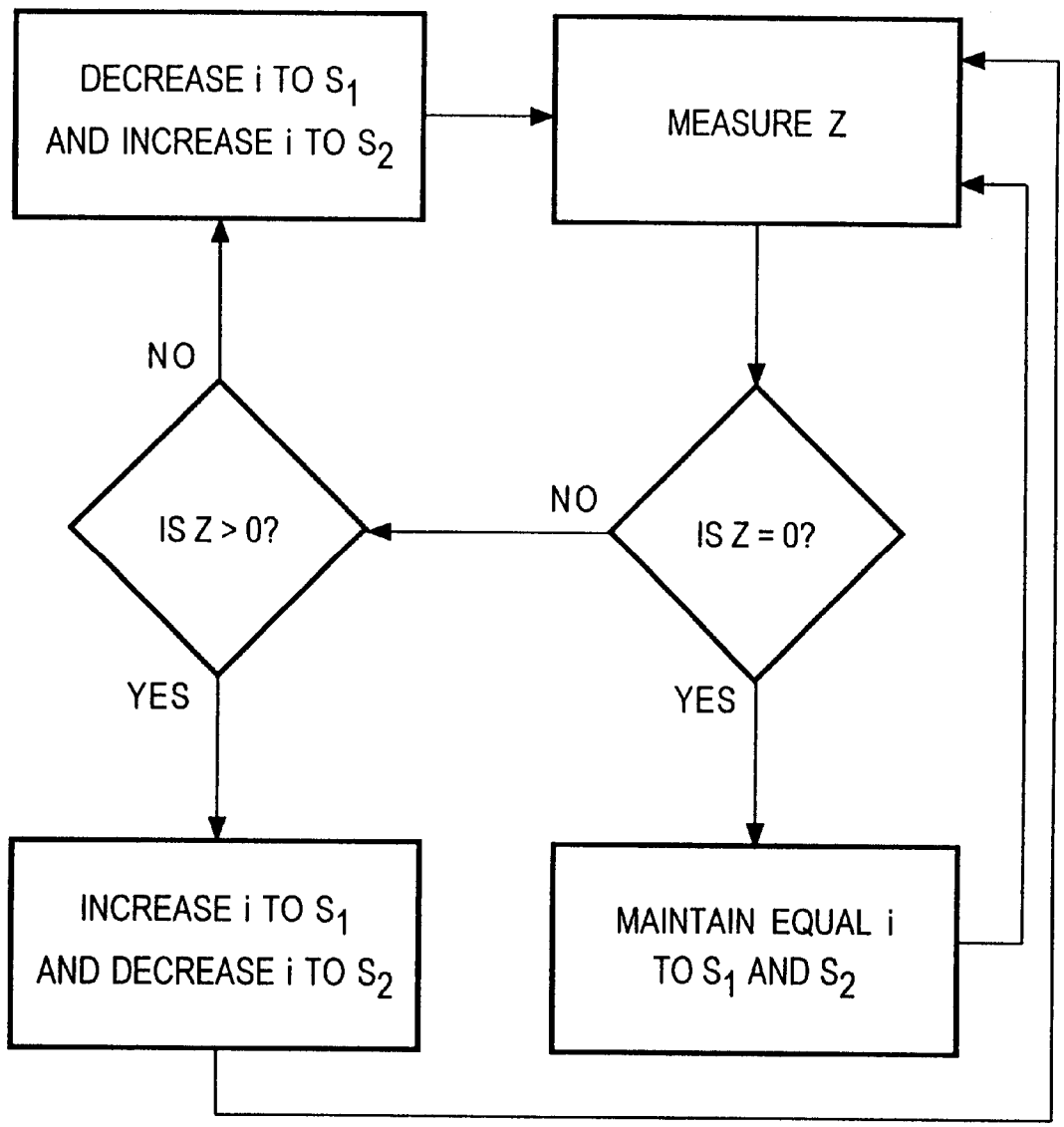
FIG. 13 is a flow chart illustrating the detection system for the impeller position.

A flow diagram illustrating one system for unbalancing the currents to provide a magnetic restoring force is set forth in FIG. 13. Referring to FIG. 13, it can be seen that z is measured. If z is equal, equal currents are maintained on stator 24 ($S_1$) and stator 26 ($S_2$). However, if z is not zero, then it is determined whether z is greater than zero. If z is greater than zero, then the current to stator 26 ($S_2$) is decreased and the current to stator 24 ($S_1$) is increased. If z is greater than zero, then the current to stator 26 ($S_2$) is increased and the current to stator 24 ($S_1$) is decreased.

It is to be understood that various methods and systems may be utilized for unbalancing the currents to the two stators for providing the magnetic restoring force and that FIG. 13 is only one of numerous methods that can be utilized.

Although illustrative embodiments of the invention have been shown and described, it is to be understood that various modifications and substitutions may be made by those skilled in the art without departing from the novel spirit and scope of the present invention.

What is claimed is:

1. A rotary blood pump, comprising:
   a pump housing;
   a rotor mounted for rotation within said housing, said rotor having an impeller;
   a rotor motor, said motor including a plurality of permanent magnets carried by said impeller and a motor stator including electrically conductive coils and pole pieces located within said housing;
   said motor being operable to transmit torque and also to provide an axial magnetic force that acts as an axial bearing.

2. A rotary blood pump as defined in claim 1, in which said rotor has a shaft portion, and including radial magnet bearings carried by said shaft portion and radial magnetic bearings carried by said housing.

3. A rotary blood pump as defined in claim 1, including a sensor for detecting axial deflection of said impeller and a circuit for energizing said stator in response to said detector.

4. A rotary blood pump, comprising:
   a pump housing;
   a rotor mounted for rotation within said housing, said rotor having an impeller;
   a rotor motor, said motor including a plurality of permanent magnets carried by said impeller, a first motor stator positioned on one side of said impeller and a second motor stator positioned on an opposite side of said impeller;
   said motor stators each including electrically conductive coils and pole pieces located within said housing;
   said motor being operable to transmit torque and also to provide an axial magnetic force that acts as an axial bearing.

5. A rotary blood pump as defined in claim 4, in which said rotor has a shaft portion, and including radial magnetic bearings carried by said shaft portion and radial magnetic bearings carried by said housing.

6. A rotary blood pump as defined in claim 4, including a detector for detecting axial movement of said impeller and a circuit for providing energization to said stators in response to said detector.

7. A rotary blood pump as defined in claim 6, in which said detector senses the axial position of said impeller, if said axial position is neutral then current to said stators is not varied, but if said axial position is other than neutral the relative currents to said first and second stators are varied to provide an axial force to return said impeller to neutral.

8. A rotary blood pump, comprising:
   a pump housing;
   a rotor mounted for rotation within said housing, said rotor having an impeller;
   a plurality of permanent magnets carried by said impeller;
   a first motor stator on one side of said impeller for coaction with said permanent magnets carried by said impeller;
   a second motor stator located on the opposite side of said impeller for coaction with said permanent magnets carried by said impeller;
   said first motor stator comprising a first plurality of coils and pole pieces;
   said second stator comprising a second plurality of coils and pole pieces;
   a circuit for energizing said first and second stators;
   a detector for detecting a position of said impeller;
   the energization of said stators being responsive to said detector for varying the position of said impeller in response to an output from said detector.

9. A method for controlling a rotary blood pump, which comprises the steps of:
   providing a pump housing;
   providing a rotor mounted for rotation within said housing, said rotor having an impeller;
   providing a rotor motor which includes a plurality of permanent magnets carried by said impeller and a motor stator; and
   operating said motor to transmit torque and also to provide an axial magnetic force that acts as an axial bearing.

10. A method as defined in claim 9, including the steps of detecting axial deflection of said impeller and energizing said stator in response to said detection.

11. A method as defined in claim 9, including the steps of providing another motor stator on an opposite side of said impeller and controlling the current to said stators in response to axial movement of said impeller.

12. A method for controlling a rotary blood pump, which comprises the steps of:
   providing a pump housing;
   providing a rotor mounted for rotation within said housing, said rotor having a shaft portion and an impeller carried by said shaft portion;
   providing a rotor motor, said motor including a plurality of permanent magnets carried by said impeller, a first motor stator positioned on one side of said impeller and a second motor stator positioned on an opposite side of said impeller;
   operating said motor to transmit torque and also to provide an axial magnetic force that acts as an axial bearing;
   detecting axial movement of said impeller; and
   providing current to said stators in response to said detection step.

13. A method as defined in claim 12, in which the detection step comprises sensing the axial position of said impeller; if the axial position is neutral then not varying current to said stators, but if said axial position is other than neutral then varying the relative currents to said first and second stators to provide an axial force to return said impeller to neutral.

14. A method of controlling a rotary blood pump, which comprises the steps of:
   providing a pump housing;
   providing a rotor for rotation within said housing, said rotor having an impeller;
   providing a plurality of permanent magnets carried by said impeller;
   providing a first motor stator on one side of said impeller for coaction with said permanent magnets carried by said impeller;
   providing a second motor stator located on the opposite side of said impeller for coaction with said permanent magnets carried by said impeller;
   energizing said first and second stators;
   detecting the axial position of said impeller;
   energizing said stators in response to said detection of said axial position of said impeller to vary the position of said impeller.

15. A method for controlling a rotary blood pump, which comprises the steps of:
   providing a pump housing;
   providing a rotor for rotation within said housing, said rotor having an impeller;
   providing a plurality of permanent magnets carried by said impeller;
   providing a first motor stator on one side of said impeller for coaction with said permanent magnets carried by said impeller;
   providing a second motor stator located on the opposite side of said impeller for coaction with said permanent magnets carried by said impeller;
   detecting the axial position of said impeller; and
   unbalancing the currents to the two stators in response to the detecting step for providing a magnetic restoring force to move the impeller axially.

* * * * *